Figures 1, 2:
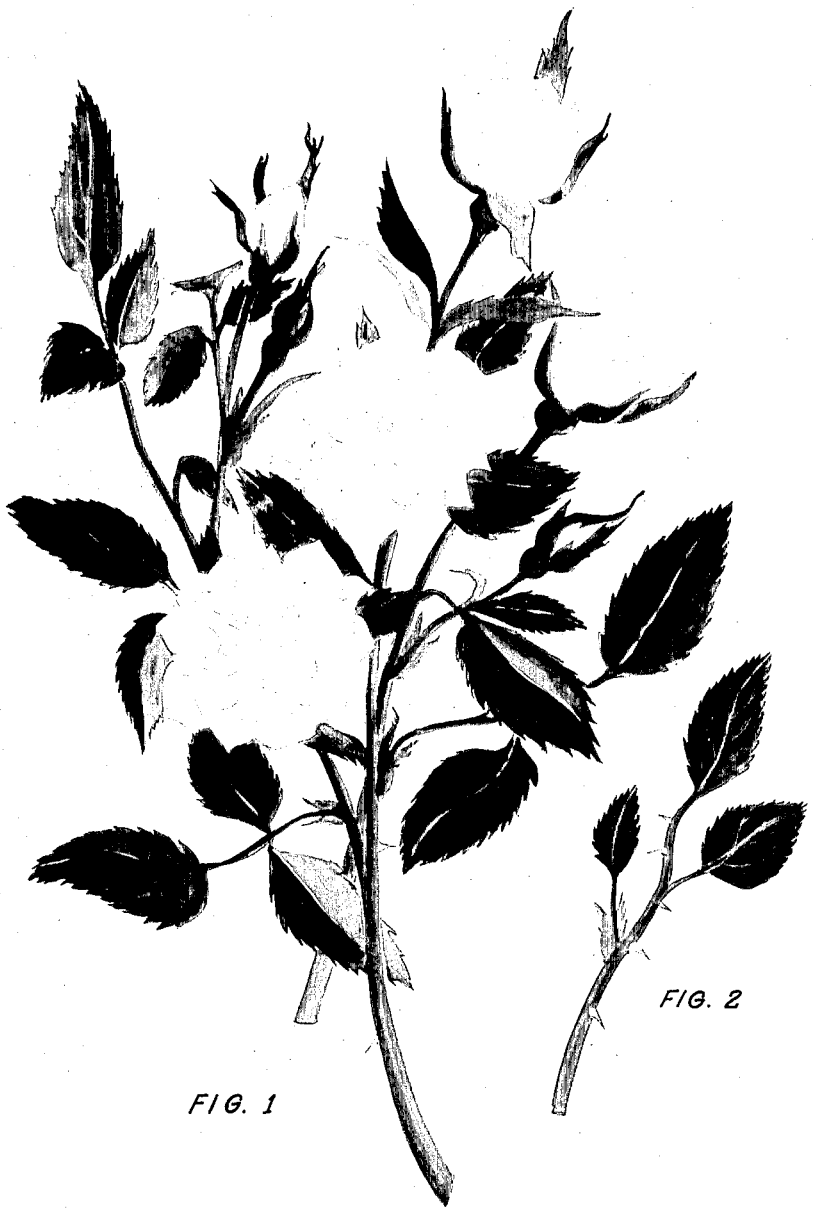

Oct. 19, 1965 R. S. MOORE Plant Pat. 2,563

MINIATURE ROSE PLANT

Filed Aug. 31, 1964

WITNESS
Jeanette Nunn Copley

INVENTOR
Ralph S. Moore

United States Patent Office

Plant Pat. 2,563
Patented Oct. 19, 1965

2,563
MINIATURE ROSE PLANT

Ralph S. Moore, 2519 E. Mineral King, Visalia, Calif.

Filed Aug. 31, 1964, Ser. No. 393,466
1 Claim. (Plt.—7)

The present invention relates to a new and distinct variety of hardy, dwarf, bush type rose plant of the hybrid miniature class; the variety being primarily characterized—as to novelty—by very double pink flowers which are similar to the Pink Cameo (Pat. 1,451) except that flowers are more double and are light pink on top side of petals with darker pink reverse.

The variety is further characterized by:

An abundance of bloom, with flowers usually borne in clusters of three to ten or more to the stem.

A plant which is vigorous, of rounded habit, with glossy, medium green leaves. The plant, which has a normal average height of about 12" at maturity, resembles the general plant habit of the Easter Morning (Pat. 2,177) miniature rose.

A plant which grows and blooms satisfactorily both in the greenhouse and outdoors; is a good plant potted; and provides excellent garden decoration as well as cut flowers.

The present variety of miniature rose was originated by me in my nursery located at Visalia, Californa, under conditions of careful control and observation, as a cross of an unnamed and unpatented seedling (*Rosa wichuraiana* × *Floradora*, both unpatented) as the seed parent and another unnamed and unpatented seedling (of complex heredity involving an unnamed climbing floribunda × Zee, both unpatented) as the pollen parent.

Subsequent to origination of the variety, I successfully asexually reproduced it, in my nursery located as aforesaid, by budding as well as by cuttings; the reproductions having run true in all respects.

The figures of the drawing illustrate a spray, including foliage, buds and flowers.

Referring now specifically to the new and distinct variety of miniature rose plant, the following is a detailed description thereof in outline; all major color plate identifications being by reference to The British Colour Council Colour Chart, except where common terms of color definition are employed.

Type: Hardy; dwarf; bush; seedling; greenhouse; outdoors; garden decoration; potted plant.

Class: Hybrid miniature (miniature).

Flowers:

*Continuity.*—Continuous.

*Fragrance.*—Slight—apple.

Flowers borne: Usually several together in compact cluster on 2" to 4" stem; strong sturdy stems.

Quantity of bloom: Average abundance both outside and in greenhouse.

Bud:

*Peduncle.*—Medium length; slender but sturdy; erect; medium green; almost smooth.

*Before calyx breaks.*—Size—small. Form—short-pointed, usually with numerous small hair-like appendages on surface of the bud; with foliaceous parts extending beyond the tip of the bud equal to one-half or more of its length. Color—medium green.

*As calyx breaks.*—Color—usually deep pink.

*As first petal opens.*—Size—small. Form—short-pointed. Color: outside—Tyrian Rose 24/2—pale yellow-green at base; inside—Tyrian Rose 24/3—shading to deeper pink near base thence into yellow at base. Opening—usually opens well and quite slowly.

Blooms:

*Size when fully open.*—Small, averaging 1".

*Petalage.*—Very double—usually 75 or more.

*Form.*—High centered and full at first, with petals rolled loosely outward, and later at maturity outer petals rolled further back, giving flower almost a ball shape.

Petals: Fairly thick; satiny both inside and outside.

*Shape.*—Outside petals broad lanceolate (almost round); intermediate — broad lanceolate with nearly round tip; inside—lanceolate with acute tip.

*Color.*—Newly opened flower from a plant grown outdoors (August 1964), Visalia, California. Outside petal: outside surface—Tyrian Rose 24/2, shading into yellow at base; inside surface—Tyrian Rose 24/3, yellow at base. Intermediate petal: outside surface—Tyrian Rose 24/2, yellow at base tip; inside surface—Tyrian Rose 24/3, yellow at base tip.

*General color effect.*—Newly opened flower: top of flower—soft pink; back side of flower—deeper pink. Three days open—soft very delicate pink.

*Behaviour.*—Hang on for a time.

*Flower longevity (May–June 1964).*—Bush in garden 4 to 7 days. Cut flowers kept at living room temperature 3 days.

Reproductive organs:

*Stamens.*—Usually none.

*Anthers.*—Usually none.

*Pollen.*—None.

*Pistils.*—Moderate number.

*Styles.*—Uneven, short, bunched.

*Stigma.*—Usually lacking, incomplete or malformed.

*Ovaries.*—All enclosed in calyx.

*Hips.*—None.

*Sepals.*—Spear shaped, nearly flat, sometimes slightly recurved usually drop off with peduncle.

*Seeds.*—None.

Foliage:

*Leaves.*—Compound of five leaflets; abundant, small, leathery; glossy.

*Leaflets.*—Shape—lanceolate; apex acute; base round (sometimes pointed).

*Margin.* — Serrate. Color — medium green; new growth usually green but sometimes lightly tinted reddish.

*Rachis.*—Medium strength; upper surface grooved with a few short hairs or prickles; under side sparsely thorny.

*Stipules.*—Medium to short; fairly narrow; short to medium length points, turning out at an angle of 45 degrees or more.

Growth:

*Habit.*—Dwarf; bushy; moderately spreading; much branched.

*Growth.*—Free; vigorous. Canes—medium, stocky. Main stems—color—medium green. Thorns—moderately thorny; long oval base; medium length; hooked slightly downward. Color — brown. Prickles—none. Hairs—none.

*Branches.*—Color—medium green. Thorns—moderately thorny; medium length; hooked slightly downward; long oval base. Color—light brown to greenish-brown.

*New shoots.*—Color—medium to bright green, sometimes lightly tinted reddish. Thorns—moderately thorny; medium length; hooked very slightly downward; long oval base. Color—reddish. Prickles—none. Hairs—none.

The miniature rose plant and its flowers as herein described may vary slightly in detail due to climatic, soil and cultural conditions under which the variety may be grown; the present description being of the variety as grown at Visalia, California.

The following is claimed:

A new and distinct variety of miniature rose plant of hardy, dwarf, rounded (or slightly spreading), much branched, bush type, as illustrated and described, characterized by buds and flowers resembling the Pink Cameo miniature rose in color and general effect but with shorter buds, and smaller more high centered very double flowers; the flowers being lighter pink with reverse darker pink;

the bush being more like that of Easter Morning but with harder textured, more glossy foliage; and further characterized by a plant which is vigorous in growth, yet compact, easy to propagate from cuttings, with small medium green foliage, an abundance of bloom, with flowers usually borne several to the stem in compact, well arranged clusters.

No references cited.

ABRAHAM G. STONE, *Primary Examiner.*